United States Patent [19]

Harding, Jr.

[11] Patent Number: 4,795,637

[45] Date of Patent: Jan. 3, 1989

[54] RODENT REPELLENT POWDERS

[76] Inventor: Norman T. Harding, Jr., 2320 Laketon Rd., Pittsburgh, Pa. 15221

[21] Appl. No.: 52,076

[22] Filed: May 21, 1987

[51] Int. Cl.$^4$ .................... A01N 25/08; A01N 59/14; A01N 65/00

[52] U.S. Cl. ................... 424/195.1; 424/148; 424/195.1; 424/197.1; 424/409; 424/410; 514/920

[58] Field of Search ............ 424/148, 410, 196.1, 424/409, 84, 195.1, 197.1; 514/920

[56] References Cited

U.S. PATENT DOCUMENTS

| | | | |
|---|---|---|---|
| 75,561 | 3/1868 | McKinsey | 424/195.1 |
| 136,185 | 2/1873 | Sears | 424/195.1 |
| 1,871,949 | 8/1932 | Bottrell | 514/711 |
| 2,159,550 | 5/1939 | Cross | 424/195.1 |
| 4,110,431 | 8/1978 | Oita | 424/148 |
| 4,654,080 | 3/1987 | Harding, Jr. | 106/270 |
| 4,668,294 | 5/1987 | Harding, Jr. | 106/237 |

FOREIGN PATENT DOCUMENTS

| | | | |
|---|---|---|---|
| 888216 | 12/1971 | Canada | 424/410 |
| 1233115 | 10/1960 | France | 424/410 |

OTHER PUBLICATIONS

E. L. Rice, Pest Control With Natures Chemicals, 7/85, pp. 16-17 and 186-187.

*Primary Examiner*—Allen J. Robinson
*Attorney, Agent, or Firm*—Buchanan Ingersoll; Lynn J. Alstadt

[57] ABSTRACT

Rodent repellent powders are disclosed which are comprised of thujone oil in a powder mixture which does not readily atomize containing at least one of the group of lime powder, borax powder, pyrethrum powder, silica gel, sulphur powder, sabadilla, pepper powder, and tobacco dust.

4 Claims, No Drawings

RODENT REPELLENT POWDERS

FIELD OF THE INVENTION

The present invention relates to powders having rodent repellent characteristics.

DESCRIPTION OF THE PRIOR ART

For many years numerous attempts have been made to keep rats and mice away from homes, storage bins and other areas. Most commonly, traps or poisons are used to kill the vermin. In addition to creating dead animal disposal problems, traps and poisons also pose dangers to children, pets and animals. Furthermore, traps and poisons must be monitored. Sprung traps must be reset and consumed poison must be replaced. Also, many people have found that for each rat they kill with traps or poison there are others in the area who survive.

Rather than try to kill the rodents which are present, a better approach is to deter them from entering the area. Certain plant extracts have been found to have repellent properties. Bottrell in U.S. Pat. No. 1,871,949 uses oil of peppermint to repel rodents. Cross in U.S. Pat. No. 2,159,550 teaches that extracts from the wood and fruit of the Areca catechu plant have repellent properties. Yet, neither of these materials have had any commercial success.

The art has also recognized that certain plants repel rodents. For example, pieces of the wormwood plant (Artemsia Absinthium) have been used as moth and rodent repellents. But, these pieces are only effective for a relatively short period of time, typically a few days.

The art has generally attributed the repellent characteristics of the wormwood and other plants to the presence of alkyloids in the plant. Apparently, these alkyloids are poisonous However, I have discovered that thujone oil, a natural oil from the cedar tree, not alkyloids, will repel rodents when used in paints or paraffin bars as described in my U.S. Pat. No. 4,654,080 issued Mar. 31, 1987 and U.S. Pat. No. 4,668,294 issued May 26, 1987. However, use of paint and paraffin bars to repel is practical for only those areas which are exposed or easily accessible. This present application sets forth a new manner to repel rodents in which the accessibility problem is overcome.

SUMMARY OF THE INVENTION

I provide a rodent repellent in a powder form by combining thujone oil with a powder which does not atomize readily when agitated. I prefer to use lime powder, borax powder, pyrethrum powder, silica gel, sulphur powder, sabadilla, pepper powder, and tobacco dust. Other powders with a density in the range of 0.9 grams/cubic centimeter to 1.0 grams/cubic centimeter and a moderately coarse particle size are also suitable.

I prefer to use a mixture comprised of between one-half and one ounce of thujone oil for every ten ounces of powder. The resulting mixture is a dense powder which does not mist or dust when applied. As a powder, this repellent is able to be applied to areas which otherwise would be too difficult to reach.

DESCRIPTION OF THE PREFERRED EMBODIMENTS

I have found that certain compositions of thujone oil and a powder mixture will repel rodents for a significant period of time. The powder which has been infused with the thujone oil can be packaged in packets which are permeable to the scent of thujone oil. It can also be spread over the target area. The effective life of the powder product usually is six months to a year depending upon the environment.

To make the powder mixture, thujone oil is first extracted from the plant source. Thujone oil can be extracted from the wormwood plant, but it is also commercially available as an ingredient for perfumes. Thujone oil can also be extracted from the cedar plant, as well as hybrid species of the wormwood plant and sage. The thujone oil is then combined with a powder mixture to form the rodent repellent powder.

I combine the thujone oil with a mixture of up to eight different powders that do not readily atomize when agitated. They are lime powder, borax powder, pyrethrum powder, silica gel, sulphur powder, sabadilla, pepper powder, and tobacco dust which can be used alone or in combination. Other powders, such as carboxymethylcellulose, which do not readily atomize when agitated can also be used.

After the powder mixture is prepared, the thujone oil is preferably added to the powder in a ratio of one (1) ounce of oil for every ten (10) ounces of powder. However, I have discovered that ratios as low as one-half (½) ounce of oil for every ten (10) ounces of powder can also be effectively used to provide a rodent repellent powder. A higher concentration of thujone oil could be used; but higher concentrations are not cost effective.

The resulting repellent powder mixture can be applied to areas which normally are inaccessible. Paint and solid bar repellent compounds cannot be effectively applied through small openings in a floor board or wall panel. But, the rodent repellent powder can be applied through any opening. The powder can be sprayed or otherwise applied through even small openings, repelling rodents and other vermin from spaces which were previously thought to be unmanageable.

One of the major advantages of my repellent powder is that the thujone oil prevents the powder mixture from misting or dusting when applied. Rather, the repellent powder is a dense mixture which will remain agglomerated when applied. The repellent powder will remain as a whole and no mist or dust cloud will form. Thus, ease of application is attained and the resulting clean-up is minimized.

While I have described certain present preferred embodiments of my invention it should be distinctly understood that the invention is not limited thereto but may be variously embodied within the scope of the following claims.

I claim:

1. A rodent repellent powder comprised of thujone oil and at least one powder selected from the group consisting of lime powder, borax powder, pyrethrum powder, silica gel, sulphur powder, sabadilla, pepper powder, and tobacco dust, wherein said rodent repellent powder contains at least one-half (½) ounce of said thujone oil for every ten (10) ounces of said powder material.

2. The rodent repellent powder of claim 1 containing from one-half (½) to one (1) ounce of said thujone oil for every ten (10) ounces of said powder mixture.

3. The repellent of claim 1 wherein the powdered material has a density between 0.9 grams/cubic centimeter and 1.0 grams/cubic centimeter.

4. The rodent repellent powder of claim 3 containing from one-half (½) to one (1) ounce of said thujone oil for every ten (10) ounces of said powdered material.

* * * * *